United States Patent

Černý et al.

[11] Patent Number: 4,720,497
[45] Date of Patent: Jan. 19, 1988

[54] 6-PURINYL N-/2-CHLOROETHYL/CARBAMATE AND THIOCARBAMATE AND PROCESS FOR THE PREPARATION THEREOF

[75] Inventors: Antonín Černý; Jiří Křepelka, both of Prague; Milan Melka, Hradec Kralova; Milan Miko, Bratislava; Stanislava Pokorna, Prague; Ružena Reichlova, Prague; Irena Kejhova, Prague; Marta Beitova, Prague; Jaroslava Grimova, Prague, all of Czechoslovakia

[73] Assignee: SPOFA, Spojene Podniky pro Zdravotnickou Vyrobu, Prague, Czechoslovakia

[21] Appl. No.: 812,139

[22] Filed: Dec. 23, 1985

[30] Foreign Application Priority Data

Dec. 22, 1984 [CS] Czechoslovakia ............ 10291-84

[51] Int. Cl.⁴ .................. C07D 473/30; A61K 31/52
[52] U.S. Cl. .................................. 514/262; 544/276; 544/265
[58] Field of Search ............. 544/265, 276; 514/262

[56] References Cited

U.S. PATENT DOCUMENTS 4,443,435  4/1984  Bodor et al. .................... 514/45

FOREIGN PATENT DOCUMENTS 0186454  7/1986  European Pat. Off. .

Primary Examiner—Nicholas S. Rizzo

[57] ABSTRACT

6-purinyl N-(2-chloroethyl) carbamate and thiocarbamate are disclosed of the general formula I,

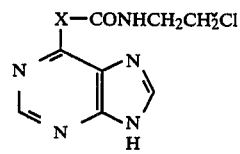

in which X stands for an oxygen or sulfur atom, and also a process for their preparation by reacting a purine derivative of the general formula II (hypoxanthine or 6-mercaptopurine, respectively) with 2-chloroethylisocyanate. The subject compounds of formula I show a remarkable antineoplastic effect in vitro and in vivo, and consequently have great potential for the treatment of malignant neoplastic diseases in mammals.

5 Claims, No Drawings

6-PURINYL N-/2-CHLOROETHYL/CARBAMATE AND THIOCARBAMATE AND PROCESS FOR THE PREPARATION THEREOF

BACKGROUND OF THE INVENTION

The invention relates to 6-purinyl N-(2-chloroethyl) carbamate and thiocarbamate of the general formula I

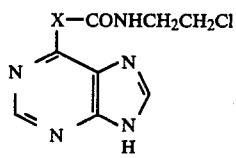

in which X stands for an oxygen or a sulfur atom, and to a process for the preparation thereof.

The relevant literature reports certain 6-purinyl derivatives of carbamic acid, e.g. N-(6-purinyl)-N'-aryl- and N'-alkylureas (A. S. Jones et al., Tetrahedron 26, 791—1970); H. Griengl et al., Arch. Pharm. 317 (3), 193, (1984)) and N-(2-chloroethyl)-6-aminopurine-9-carboxamide formed by reacting 2-chloroethylisocyanate with adenine (Miyahara Michiko et al., Eisai Shikenako Hokoku 1980 (98), 123–5; Chem. Abstr. 94, 114381w (1981)). The named compounds did not exhibit any biological activity with the exception of some adenine urea derivatives, e.g. N-(6-purinyl)-N', N'-diethylurea, which showed a weak antineoplastic action. The compounds of their present invention, 6-purinyl esters of N-(2-chloroethyl) carbamic acid, represent a new, previously not described class of compounds which surprisingly demonstrate a remarkable antineoplastic activity both in vitro and in vivo.

SUMMARY OF THE INVENTION

The subject compounds of formula I can be prepared by reacting the respective 6-substituted puring derivative of the general formula II

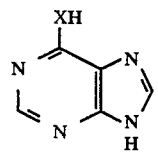

in which X has the above defined meaning with 2-chloroethylisocyanate of formula III

in an inert medium at a temperature substantially within the range from 0° to 50° C., preferably in the present of an alkaline agent.

The starting purine derivatives of formula II, i.e. hypoxanthine (X=O) and 6-mercaptopurine (X=S), are commercially available materials. The preparation of 2-chloroethylisocyanate is described in several places in the literature (cf. e.g. Siefken W., Ann. Chem. 562, 103—1949).

Suitable inert media for the aforementioned reaction are advantageously dimethylformamide, dimethylsulfoxide, phosphopric acid hexamethyltriamide or tetramethylurea.

The reaction of hypoxanthine or 6-mercaptopurine with 2-chloroethylisocyanate proceeds rather slowly; yet, suprisingly, it is unexpectedly accelerated in the presence of one to two molar equivalents of an alkaline agent, preferably a tertiary organic amine such as, e.g., triethylamine, diisopropylethylamine, 1-ethylpiperidine, 4-methylmorpholine or the like, whereby the reaction rate is increased approx. by an order of magnitude and also the yield of the desired product is substantially improved.

The compounds of the invention are either slightly soluble in the aforementioned solvents and separated spontaneously from these media during the reaction, or can easily be isolated from the reaction mixture by dilution with water and subsequent filtration.

The subject compounds of the general formula I, e.g. 6-[N-(2-chloroethyl)carbamoyl]thiopurine (compound Ia, X=S) and its oxygen analogue, 6-N-[(2-chloroethyl)carbamoyl]oxypurine (compound Ib, X=O) display a remarkable antineoplastic activity in pharmacological experiments both in vitro and in vivo in experimental animals, and consequently have potential for the treatment of malignant neoplastic diseases of biological subjects, especially of mammalian origin, when administered either alone or in combination with other agents having an antineoplastic activity.

The antineoplastic activity of the compounds of the invention has been investigated by testing the compounds of the chemical group "in vivo" against experimental rodent tumors such as Crocker's sarcoma (S180), solid-type Ehrlich carcinoma (STE), kreb's ascites tumor (Kr2), all maintained in mice H, Gardner lymphosarcoma (LsG, C3H mice), P388 and L1210 leukemias (DBA2 mice), Zajdela ascites hapatoma (ZAH, Wistar rats), Yoshida ascites reticulosarcoma (Y, Wistar rats) and B16 melanoma (C57B16 mice) in experiments according to Jelinek, V. (Neoplasma 12, 469 (1969); ibid. 7, 146 (1960) and "in vitro" experiments using radioactive precursors of nucleic acids and proteins according to Miko, M. et al. (Cancer Res. 39, 4242 (1979); Neoplasma 26, 449 (1979); ibid. 16, 161—1969) with minor modifications (Mattern J.: Studies on the Drug Sensitivity of Short Term Cultured Tumor Cell Suspensions. In "Human Tumors in Short Term Culture" (Dendy, P. P. ed.), p. 301, Academic Press 1976). Therapeutic synergism has been studied by the method of Carter, W. H. et al. (cf. Cancer Res. 42, 2963—1982).

The therapeutic effect for the purposes of the invention means the inhibition of characterstic disease symptoms in biological subjects bearing tumors which are namely the tumor growth, shortening of the survival period of biological subject and increasing the number or the growth of tumor cells. Tumor growth may be observed clinically or in experiments "in vivo", that is, with experimental animals, or "in vitro", for example, in tissue cultures prepared from tumors. The assessment of tumor growth may be effected by measuring the weight of the tumor mass or, more effectively, by measuring the weight of the tumor mass or, more effectively, by measuring the radioactivity after incorporation therein of certain substances of natural origin such as amino acids (for example, valine), nucleic bases or the like (thymidine etc.) labeled with radioactive atoms such as $^{14}C$, $^{3}H$ etc.

Such a useful therapeutical effect of the compounds of the present invention has been proven in experiments with S180 and/or STE tumor bearing female mice H. In comparison with untreated control animals, significantly lower mean tumor weights have been observed in treated groups of animals (cf. Examples 3 and 4).

Additionally, the compounds of the present invention are useful in increasing survival time of the suitable biological subjects, namely mice and rats bearing tumors STE, ZAH and/or Y: because of the lethal nature of the test system employed, the antitumor effect of the compounds is illustrated by a side comparison of the survival time of treated animals (survival for a longer time) with the untreated control groups of animals (cf. Examples 5, 6, and 7). In these typical experiments, ten animals are in the experimental groups, and the treated groups of animals survive for a longer time than the untreated controls.

Moreover, in some cases the antitumor effect of the compounds of the present invention has been proven in experimental conditions in which the clinically useful and structurally similar compound 6-mercaptopurine is inactive (cf. Example 8). The result of the experiment is in agreement with the concept that mechanism of action of the compound Ia is different from that of clinically used 6-mercaptopurine. This effect may be clinically useful in all cases of the resistance of the tumor or leukemia against an antimetabolite of this class.

Additionally, the therapeutic synergism of the compounds of the general formula I with other cytostatic drugs has been proven, for example, in combination chemotherapy with Benfluron (5-[2-(N, N-Dimethylamino)ethoxy]-7-oxo-7H-benzo(c)fluorene hydrochloride—CAS 80427-58-3)—cf. Example 9. The groups of animals treated by combination of the compound Ia with cytstatic drug Benfluron survive for a highly significantly longer period ($P \leq 0.01$) than the untreated animals of the control groups or animals treated with benfluron alone. The foregoing examples indicate that the comound Ia may be effectively used alone or in combination with other cytostatic drugs for treatment of malignant neoplastic diseases.

In experiments in vivo with Ehrlich ascites carcinoma cells and/or Yoshida ascites tumor cells, the compound Ia has been more effective than some clinically sued drugs, namely, thioguanine (2-Amino-6-mercaptopurine, NSC 752) and/or 6-mercaptopurine (NSC 755), cf. Examples 10 and 11.

The compounds of the present invention are also potent inhibitors of DNA and protein biosyntheses of tumor cells. This conclusion clearly follows from Example 12. Inhibition of any of the vital biosynthesis mentioned above is attainable as a result of antitumor activity of cytostatic drugs.

The compounds described herein can be administered to suitable biological subjects, particularly mammals, for their therapeutic antitumor effects, by conventional modes of administration alone, but preferably as active ingredients with any conventional suitable non-toxic pharmaceutical carrier, dissolved or suspended, for example, in water, saline, polyethylene or polypropylene alcohols, etc. The administration is preferably by the oral route. The dosage administration is preferably by the oral route. The dosage administered will be dependent upon the type of tumor for which treatment is desired, the type of biological subject involved, weight, body surface, localization of the tumor, its morphological type, the frequency of treatment, individual tolerance and responsiveness of each subject, etc; for example, by oral route, the prolonged administration of 100, 200 mg/kg daily appears to be well tolerated both in the rat and in the mouse. The assessment drawn from the biological tests is that doses of 20 mg/kg (e.g. about 740 mg/m$^2$) may be regarded as well tolerated in man. The compounds are hardly toxic; for example, the compound Ia is practically non-toxic (the $LD_{50}$ in small rodents was assessed up to 3 g/kg by oral route).

It is understood that therapeutically useful effects can be expected to occur upon the administration of such doses that are completely non-toxic to the respective mammalian organism.

The process for preparing the subject compounds of formula I, as well as their selected biological assay results, are illustrated by the subsequent non-limitative examples. Melting points are determined on Kofler block and are not corrected; yields are indicated in stoichiometric percentage of theoretical amount.

DESCRIPTION OF THE PREFERRED EMBODIMENTS

EXAMPLE 1

6-[N-(2-Chloroethyl)carbamoyl]thiopurine (Ia)

A suspension of 6-mercaptopurine monohydrate (17.0 g, 0.1 mole) in dimethylformamide (150 ml) is treated with triethylamine (10.1 g, 0.1 mole) and the solid is dissolved by warming of the mixture to 50°–60° C. The solution is cooled to 15° C. and 2-chloroethylisocyanate (11.6 g, 0.11 mole) is dripped in under cooling with tap water to 15°–20° C. The reaction mixture is stirred at this temperature for 2 hours, and the precipitated product is collected on filter, washed with acetone and dried under reduced pressure at a temperature of approx. 50° C. to give 20.7 g (80%) of the title compound Ia, melting at 221°–223° C. UV absorption spectrum (in dimethylsulfoxide), $\lambda$ max 326 nm (log $\epsilon$4.33).

EXAMPLE 2

6-[N-(2-Chloroethyl)carbamoyl]oxypurine (Ib)

To a suspension of hypoxanthine (6.8 g, 50 mmoles) in dimethylformamide (200 ml) there is added triethylamine (5.05 g, 50 mmoles) and then at 15° to 20° C., 2-chloroethylisocyanate (5.8 g, 55 mmoles is dripped in. The reaction mixture is stirred at this temperature until dissolution of the solid (approx. for 2 hours), thereafter poured into an ice-water mixture (750 ml), the precipitate of the title product is separated by suction, washed with acetone and dried at room temperature. The yield is 8.2 g (67.8%) of compound Ib, m.p. 320°–240° C. (with decomposition), UV absorption spectrum (in dimethylsulfoxide), $\lambda$ max 275 nm (log $\ominus$3.76).

EXAMPLE 3

An illustration of the antitumor activity of the substance Ia

Sixty female mice H weighing approximately 20 g are divided into three groups: one control group and two experimental groups of 20 animals each. A lethal dose of the Crocker tumor (S180) homogenate is implanted subcutaneously in all the animals. The experimental groups are treated with the substance Ia in water suspension. The suspension contains the substance Ia in such an amount that a dose 0.4 or 0.2 ml of the suspension p.o. is equal to a dose 200 or 100 mg Ia/kg. This dose is administered to the experimental animals once a day, eight times altogether, starting on the fifth day after the implantation. On the fourteenth day after the implantation, a half of the animals in each group is sacrificed in ether anaesthesia, and tumors are removed and weighed. The remaining animals are left to monitor the time of death. Statistically significantly lower average values of the tumor weight are observed in the treated animals in comparison with the non-treated control group.

EXAMPLE 4

An illustration of the antitumor activity of the substances Ia and Ib

In analogous experiments carried out on the animals with implanted Ehrlich tumor (STE) (female mice H weighing approximately 20 g, 20-animals groups) the treated animals exhibit statistically significantly lower average values of the tumor weight in comparison with the non-treated control group. The results of the experiments are summarized in the following table.

| Substance | Administration | Dose mg/kg | Tumor weight (% of control) |
|---|---|---|---|
| Ia | p.o. | 8 × 200 | 70[1] |
|  |  | 8 × 100 | 80[1] |
| Ib | p.o. | 8 × 200 | 81[1] |
|  |  | 8 × 100 | 76[1] |

[1]Statistically significant difference against the control (t-test, $p \leq 0.05$)

EXAMPLE 5

An illustration of the therapeutic effect of the substance Ia

Fifty infantile female Wistar rats weighing approximately 60 g are divided into five groups: one control and four experimental ones, 10 animals each. A lethal dose of the tumor ascites from Zajdel ascitic hepatoma is implanted intraperitoneally in all the animals. The experimental groups are treated with the substance Ia in water suspension. The suspension contains the substance Ia in such an amount that a dose of 0.4 or 0.2 ml of the suspension p.o. is equal to a dose of 200 or 100 mg Ia/Kg. This dose is applied to the experimental animals once a day, five times altogether, starting on the first day after the implantation. The results are summarized in the following table.

| Substance | Administration | Dose (mg/kg) | Period of survival (% of control) |
|---|---|---|---|
| Ia | p.o | 5 × 200 | 126[1] |
|  |  | 5 × 100 | 117[1] |

[1]Statistically significant difference against the control (t-test, $p \leq 0.05$).

EXAMPLE 6

An illustration of the therapeutic effect of the substances Ia and Ib in comparison with 6-mercaptopurine (NSC 755)

An analogously performed experiment in the animals with implanted Yoshida tumor (infantile female Wistar rats weighing approximately 60 g, 10 animals per group) proves a statistically significantly higher average value of the survival period in the treated animals in comparison with the non-treated control group. The results of the experiment are summarized in the following table.

| Substance | Administration | Dose (mg/kg) | Period of Survival (% of control) |
|---|---|---|---|
| 6-mercapto-purine | p.o. | 5 × 40 | 127[1] |
|  |  | 5 × 20 | 109 |
| Ia | p.o. | 5 × 200 | 127 |
|  |  | 5 × 100 | 134[1] |
| Ib | p.o. | 5 × 200 | 83 |
|  |  | 5 × 100 | 100 |

[1]Statistically significant difference against the control (t-test, $p \leq 0.05$).

EXAMPLE 7

An illustration of the therapeutic effect of the substance Ia in comparison with 6-mercaptopurine (NSC 755)

An analogously performed experiment in the animals with implanted Yoshida tumor (infantile female Wistar rats weighing approximately 60 g, 10 animal per group) proves a statistically significantly higher average value of the survival period in the treated animals in comparison with the non-treated control group. The results of the experiment are summarized in the following table.

| Substance | Administration | Dose (mg/kg) | Period of survival (% of control) |
|---|---|---|---|
| 6-mercapto-purine | p.o. | 5 × 40 | 156[1] |
|  |  | 5 × 20 | 107 |
| Ia | p.o. | 5 × 200 | 158[1] |
|  |  | 5 × 100 | 124 |

[1]Statistically significant difference against the control (t-test, $p \leq 0.05$).

EXAMPLE 8

An illustration of the therapeutic effect of the substance Ia in an experiment in which a distantly similar 6-mercaptopurine proves ineffective An experiment analogous to the Examples 5 to 7 performed in animals with implanted Zajdel ascitic hepatoma (imfantile female Wistar rats weighing approximately 60 g, 10 animals per group) proves a statistically significantly higher average period of survival in the animals treated with the substance Ia but not in those treated with 6-mercaptopurine, in comparison with non-treated control group. The results of the experiment are summarized in the following table.

| Substance | Administration | Dose (mg/kg) | Period of survival (% of control) |
|---|---|---|---|
| 6-mercapto-purine | p.o. | 5 × 40 | 105 |
|  |  | 5 × 20 | 101 |
| Ia | p.o. | 5 × 200 | 128[1] |
|  |  | 5 × 100 | 120[1] |

[1]Statistically significant difference against the control (t-test, $p \leq 0.05$)

EXAMPLE 9

An illustration of the therapeutic synergism of the substance Ia with other cytostatic drugs One hundred and twenty seven infantile female Wistar rats weighing 50–60 g are divided into sixteen groups: one control group of 25 animals and fifteen experimental groups of 6 to 7 animals. A lethal dose of the tumor ascites from Yoshida ascitic sarcoma is implanted intraperitoneally in all the animals. The experimental groups are treated with the substance Ia in water suspension, water solution of a cytostatic Benfluron (CAS 80427-58-3), or a combination of both the substances. The suspension or solution contains the substances in such a concentration that doses of 0.4 or 0.2 and 0.1 ml of the suspension/solution p.o. are equal to doses of 200 or 100 and 50 mg Ia/kg or to doses of 160, 80 or 40 mg of Benfluron/kg. Doses of the substance Ia are administered to the experimental animals once a day, four times altogether, starting on the first day after the tumor implantation. Benfluron is administered only once, on the fourth day after the tumor implantation, 7 hours after the last dose of the substance Ia. Over a period of 29 days it is observed that all the animals in the control group die on the 5th to 15th days after the implantation, while the groups treated with the substance Ia or with its combination with cytostatic Benfluron survive longer, with an average statistical significance ($\alpha=0.05$) or a high statistical significance ($\alpha=0.01$). The results of the experiment are summarized in the following table.

| Dose (mg/kg p.o.) | | Average period of survival | | |
|---|---|---|---|---|
| Ia | Ben-fluron | (days) | (% of control) | Notes |
| 0 | 0 | 7.34 (6.8; 7.9) | 100 | |
| 4 × 200 | 0 | 8.86 (7.4; 10.7) | 121 | |
| 4 × 100 | 0 | 10.94 (9.0; 13.3) | 149 | (2) |
| 4 × 50 | 0 | 9.20 (7.6; 11.1) | 125 | (1) |
| 0 | 160 | 7.79 (6.9; 8.8) | 106 | |
| 0 | 80 | 7.61 (6.5; 8.9) | 104 | |
| 0 | 40 | 7.67 (6.9; 8.6) | 104 | |
| 4 × 200 | 160 | 17.18 (10.9; 26.9) | 234 | (2) |
| 4 × 200 | 80 | 13.09 (8.8; 19.5) | 178 | (1) |
| 4 × 200 | 40 | 8.26 (6.3; 10.9) | 113 | |
| 4 × 100 | 160 | 12.97 (8.9; 19.0) | 177 | (1) |
| 4 × 100 | 80 | 14.07 (9.7; 20.4) | 192 | (2) |
| 4 × 100 | 40 | 13.97 (9.5; 20.6) | 190 | (2) |
| 4 × 50 | 160 | 20.85 (14.5; 29.9) | 284 | (2), (3), (4) |
| 4 × 50 | 80 | 8.96 (8.1; 10.0) | 122 | (2) |
| 4 × 50 | 40 | 11.39 (8.2; 15.8) | 155 | (1), (4) |

(1) Statistically significant difference against the control group ($\alpha = 0.05$)
(2) Statistically highly significant difference against the control group ($\alpha = 0.01$)
(3) Statistically highly significant difference against the group with an optimal monotherapy (4 × 100 mg Ia/kg p.o., t-test $\alpha = 0.01$)
(4) The animals surviving the 29th day sacrificed without the tumor
Fiducial limits of the geometric average for $P = 1 - \alpha = 0.95$ are given in parentheses.

EXAMPLE 10

Cytotoxicity of the substance Ia in vitro in comparison with 2-amino-6-mercaptopurine (NSC 752)

The degree of influence on the incorporation of $^{14}C$ from adenine-$^{14}C$ and valine-$^{14}C$ to the fraction of Ehrlich Carcinoma cells insoluble in trichloroacetic acid serves as the measure of cytotoxicity. The value $ID_{50}$ is the concentration of a cytostatic that reduces the $^{14}C$ incorporation down to 50% of the non-influenced control cells. The results of the experiment are summarized in the following table.

| Substance | Precursor | $ID_{50}$ ($\mu$mol/l) |
|---|---|---|
| Ia | adenine-$^{14}C$ | 94 |
|  | valine-$^{14}C$ | 155 |
| 2-amino-6-mercaptopurine | adenine-$^{14}C$ | >600 |
|  | valine-$^{14}C$ | >600 |

EXAMPLE 11

Cytotoxicity of the substance Ia in vitro in comparison with 6-mercaptopurine (NSC 755)

In analogous experiments, the degree of influence on the initial velocity of the incorporation of $^{3}H$ from 5-iodo-2′-deoxy-(6-$^{3}H$)uridine or that of $^{14}C$ from a mixture of L-(U-$^{14}C$)-aminoacids to the fraction of Yoshida ascitic tumor cells insoluble in trichloroacetic acid serves as the measure of cytotoxicity. The value $IC_{50}$ is the concentration of a substance that reduces the initial velocity of the $^{3}H$ or $^{14}C$ incorporation down to 50% of the noninfluenced control cells. The results are summarized in the following table.

| Substance | Precursor | $IC_{50}$ ($\mu$mol/l) |
|---|---|---|
| 6-mercaptopurine | 5-iodo-2′-deoxy(6-$^{3}H$)uridine | >10000 |
|  | L-(U-$^{14}C$)aminoacides | >229 |
| Ia | 5-iodo-2′-deoxy(6-$^{3}H$)uridine | 25 |
|  | L-(U-$^{14}C$)aminoacids | 26 |

EXAMPLE 12

Comparison of the cytotoxicity of the substance of Ia and Ib in vitro

In analogous experiments, the following values of $IC_{50}$ were determined:

| Substance | Precursor | $IC_{50}$ ($\mu$mol/l) | Fiducial limits ($P = 0.95$) |
|---|---|---|---|
| Ia | 5-iodo-2′-deoxy(6-$^{3}H$)uridine | 39 | (21; 106) |
| Ib | 5-iodo-2′-deoxy(6-$^{3}H$)uridine | 55 | (47; 65) |
| Ia | L-(U-$^{14}C$)aminoacids | 62 | (24; 8.10$^3$) |
| Ib | L-(U-$^{14}C$)aminoacids | 80 | (66; 104) |

We claim:
1. 6-Purinyl N-(2-chloroethyl)carbamate and thiocarbamate of the formula I

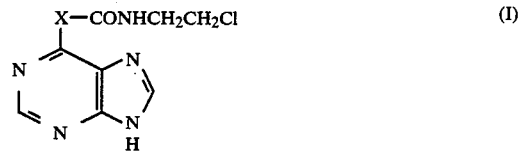

in which X stands for a bivalent uni-atomic link selected from the group consisting of an oxygen and sulfur atom.
2. 6-[N-(2-Chloroethyl)carbamoyl]oxypurine.
3. 6-[N-(2-Chloroethyl)carbamoyl]thiopurine.
4. Method for the treatment of malignant neoplastic diseases, comprising administering to a biological subject, an antineoplastic effective amount of a compound according to claim 1.
5. Process for the preparation of the compounds according to claim 1, comprising reacting the respective 6-substituted purine derivative of formula II

in which X has the above defined meaning with 2-chloroethylisocyanate

in an inert medium at a temperature from 0° to 50° C.

* * * * *